United States Patent [19]

Walker et al.

[11] Patent Number: 4,572,899

[45] Date of Patent: Feb. 25, 1986

[54] AQUEOUS SOLUTION FOR SUSPENDING AND STORING CELLS, ESPECIALLY ERTHROCYTES

[75] Inventors: Wolfram H. Walker, Rödermark; Karlheinz Gänshirt, Dreieich, both of Fed. Rep. of Germany

[73] Assignee: Biotest-Serum-Institut GmbH, Frankfurt, Fed. Rep. of Germany

[21] Appl. No.: 511,434

[22] Filed: Jul. 6, 1983

[30] Foreign Application Priority Data

Jul. 7, 1982 [DE] Fed. Rep. of Germany ....... 3225408

[51] Int. Cl.$^4$ .......................... A01N 1/02; A61K 35/14
[52] U.S. Cl. ...................................... 436/18; 424/101; 435/2; 435/240; 436/16; 436/17
[58] Field of Search .................... 424/101; 435/2, 240; 436/8, 16, 17, 18

[56] References Cited

U.S. PATENT DOCUMENTS

| | | |
|---|---|---|
| 4,255,256 | 3/1981 | Ferrante et al. ..................... 210/730 |
| 4,267,269 | 5/1981 | Grode et al. ............................ 435/2 |
| 4,299,726 | 11/1981 | Crews et al. ......................... 252/408 |
| 4,356,172 | 10/1982 | Nakao et al. ......................... 424/101 |
| 4,476,221 | 10/1984 | Kane et al. ............................... 435/2 |

*Primary Examiner*—Herbert S. Cockeram
*Attorney, Agent, or Firm*—Sprung, Horn, Kramer & Woods

[57] ABSTRACT

An aqueous solution for suspending and storing cells, especially erythrocytes, and containing sodium chloride, glucose or fructose, adenine, and a sugar alcohol, the sugar alcohol being sorbitol or xylitol is employed to further improve the storage time and hence the survival rate of the cells and even reduce the hemolysis rate of erythrocytes in packed red blood cells.

9 Claims, No Drawings

AQUEOUS SOLUTION FOR SUSPENDING AND STORING CELLS, ESPECIALLY ERTHROCYTES

BACKGROUND OF THE INVENTION

The invention is an aqueous solution for suspending and storing cells, especially erythrocytes, and containing sodium chloride, glucose or fructose, adenine, and a sugar alcohol.

Packed red blood cells are obtained in the field of blood-component therapy from whole blood containing anticoagulent from which plasma has been removed. Packed red blood cells are presently being applied in a wide range of therapeutic applications, the indication being anemia or red blood cell deficiency. Since some of the anticoagulant constituents are also removed when the plasma is separated, attempts have been made to increase the concentration of these constituents in order to maintain the storage time of the packed red blood cells as long as that of whole blood. It is also known that a subsequent addition of a suspending solution to packed red blood cells will dilute them, lowering the viscosity to a desirable level and facilitating the transfusion of the solution. Such an addition also allows specific substances necessary for the storageability of the packed red blood cells to be added to increase their rate of survival in vitro and in vivo.

Various solutions are appropriate for suspending and storing cells, especially erythrocytes. U.S. Pat. No. 4,267,269 for example discloses a solution that contains, in addition to sodium chloride, glucose or fructose, and adenine, the sugar alcohol mannitol.

Although the addition of suspending solutions to packed red blood cells does prolong storage time and hence increase the survival rate of the erythrocytes, the improvement, and especially the rate of hemolysis, the speed at which hemolysis occurs, is still not completely satisfactory.

SUMMARY OF THE INVENTION

The present invention is intended to further improve the storage time and hence the survival rate of the cells and even reduce the hemolysis rate of erythrocytes in packed red blood cells.

This objective is achieved in accordance with the invention by employing a solution in which the sugar alcohol is either sorbitol or xylitol.

It has, surprisingly, been discovered that a solution for suspending and storing cells, especially erythrocytes, will increase the survival rate and, especially, reduce the hemolysis rate of erythrocytes when it contains either sorbitol or xylitol as the sugar alcohol instead of mannitol. The hemolysis rate is a significant parameter for determining the quality of the erythrocytes. By homolysis rate the speed of hemolysis is meant. It should be as low as possible.

The beneficial properties of such a solution can be increased even more by the addition of guanosine, either alone or in combination with one or more phosphates. A hydrogenorthophosphate with a dihydrogenorthophosphate, which acts as a buffer, is especially appropriate.

The storage time of the erythrocytes can be even further prolonged by adding a colloid like modified gelatin, dextran, hydroxyethyl starch, or albumin serum to the solution (cf. Ullmann, 4th Ed., Vol. 8 [1974], pp. 634–640).

Typical solutions may be composed of 0.5–10 g of sodium chloride, 0–5 g of dibasic sodium phosphate, 0–5 g of monobasic sodium phosphate, 0.5–20 g of glucose or fructose, 1–20 g of sorbitol or xylitol, 0.05–1 g of adenine, 0–1.5 g of guanosine, and 0–10% colloids—preferably 2.5–6.5 g of sodium chloride, 0.7–2.5 g of dibasic sodium phosphate$\times 2H_2O$, 0.7–2.5 g of monobasic sodium phosphate, 5–15 g of glucose or fructose, preferably glucose monohydrate, 5–15 g of sorbitol or xylitol, preferably sorbitol, 0.1–0.5 g of adenine hydrochloride, and 0.1–0.5 g of guanosine dissolved in water for injections per 1000 ml.

Especially preferred are 4.2 g of sodium chloride, 1.14 g of dibasic sodium phosphate$\times 2H_2O$, 1.11 g of monobasic sodium phosphate$\times H_2O$, 9.4 g of glucose monohydrate, 10.0 g of sorbitol, 0.25 g of adenine hydrochloride, and 0.4 g of guanosine.

The usual way of working with this solution is to first prepare whole blood stabilized with an ACD, CPD, or heparin solution (USP XX [1980], pp. 49–50). The whole blood unit is then centrifuged and the plasma separated. Next, a suspending solution is added, preferably in a closed system of several bags, to the packed red blood cells to wash it or store it. About 50–250 ml of suspending solution can be added in one or more portions to about 200–300 ml of packed red blood cells with a hematocrit of 60–85, for example. The mixture can then be stored in a refrigerator like conventional packed blood or or even immediately transfused.

The solutions in accordance with the invention can also be employed to wash and preserve erythrocytes. They are also appropriate for transfusion. When the solutions are employed for washing, 50–250 ml and preferably 70 ml are added to 250 ml of packed red blood cells, for example. The mixtures are centrifuged and the top layer separated. Since the process can be repeated two or three times, as much as 210 ml of the solution may be necessary for washing. The packed red blood cells can subsequently be stored along with the suspending solution or even immediately transfused, with or without the suspending solution.

EXAMPLE 1

Preparing a suspending solution 4.2 g of sodium chloride, 1.14 g of dibasic sodium phosphate$\times 2H_2O$, 1.11 g of monobasic sodium phosphate$\times H_2O$, 9.4 g of glucose monohydrate, 10.0 g of sorbitol, 0.25 g of adenine hydrochloride, and 0.4 g of guanosine were weighed in separate containers. Approximately one half of 1000 ml of water for injections (aqua ad injectabilia, Ph. Eur.) was introduced into a sterilized double-walled batch boiler and heated to approximately 40° C. The weighed constituents were added over 5 minutes while being stirred and the rest of the water was added over 15 minutes with continued stirring. The temperature was simultaneously maintained at 40° C. The solution was sterilized by filtration through a 0.2 $\mu m$ membrane filter into containers from which it was pumped into individual plastic bags.

EXAMPLE 2

500 ml of blood was stabilized with 70 ml of CPD anticoagulant solution in a threefold blood-bag system. The packaged blood was chilled to approximately 6° C. and centrifuged 24 hours later. Approximately 250 ml of plasma was then transferred into an empty bag. Approximately 90 ml of suspending solution prepared as describe in Example 1 was added for the satellite bag to the packed red blood cells, the resulting volume being about 340 ml.

This mixture exhibited especially satisfactory hemolysis rates, comparable to those of the original packed blood stored under the same conditions. The suspending solution had typical storage times of 5-6 weeks at approximately 6° C.

What is claimed is:

1. Aqueous solution for suspending and storing cells, especially erythrocytes, and containing per liter 0.5-20 g of sodium chloride, 0.5-20 g of glucose or fructose, 0.05-1 g of adenine, guanosine in up to 1.5 g, 0-5 g of at least one phosphate and 1-20 g of sorbitol or xylitol.

2. A solution according to claim 1 containing sorbitol.

3. A solution according to claim 1 wherein at least one of said phosphates is hydrogenorthophosphate or a dihydrogenorthophosphate.

4. A solution according to claim 2 comprising 4.2 g of sodium chloride, 1.14 g of dibasic sodium phosphate$\times 2H_2O$, 1.11 g of monobasic sodium phosphate$\times H_2O$, 9.4 g of glucose monohydrate, 10.0 g of sorbitol, 0.25 g of adenine hydrochloride, and 0.4 g of guanosine per liter of water for injections.

5. A solution according to claim 1 additionally containing a colloid.

6. A composition comprising erythrocytes and the aqueous solution of claim 1.

7. A composition according to claim 6 wherein said aqueous solution contains sorbitol.

8. A process for washing erythrocytes which comprises mixing said erythrocytes with the solution of claim 1, thereafter removing at least a portion of said solution, and recovering the erythrocytes.

9. A solution according to claim 1, wherein at least one of said phosphates is dibasic sodium phosphate or monobasic sodium phosphate.

* * * * *